US005786152A

United States Patent [19]

Marengère et al.

[11] Patent Number: 5,786,152
[45] Date of Patent: Jul. 28, 1998

[54] METHODS OF INHIBITING SYP BINDING TO A CTLA-4 RECEPTOR

[75] Inventors: Luc Edgar Joseph Marengère, Toronto; David Peter Siderovski, Richmond Hill; Tak Wah Mak, Toronto, all of Canada

[73] Assignee: Amgen Inc., Thousand Oaks, Calif.

[21] Appl. No.: 638,271

[22] Filed: Apr. 26, 1996

[51] Int. Cl.$^6$ .................. G01N 33/53; G01N 33/566
[52] U.S. Cl. .................. 435/7.1; 435/7.21; 435/7.24; 530/351; 530/350; 530/300
[58] Field of Search .................. 435/7.21, 7.1, 435/7.24, 21; 530/351, 300, 350

[56] References Cited

U.S. PATENT DOCUMENTS

| | | | |
|---|---|---|---|
| 5,434,131 | 7/1995 | Linsley et al. | 514/2 |
| 5,580,979 | 12/1996 | Bachovchin | 540/509 |
| 5,607,974 | 3/1997 | Droge et al. | 514/562 |

OTHER PUBLICATIONS

Mahalingam et al., T cell activation and disease severity in HIV infection, Clin. Exp. Immunol., 93: 337–343, Sep. 1993.
Brunet et al., A new member of the immunoglobulin super-family—CTLA–4, Nature 328: 267–270 (16 Jul. 1987).
Green et al., Absence of B7-Dependent Responses in CD28-Deficient Mice, Immunity, 1:501–508 (Sep. 1994).
Gribben et al., CTLA4 mediates antigen-specific apoptosis of human T cells, Proc. Natl. Acad. Sci. USA, 92: 811–815 (Jan. 1995).
Harper et al., The Journal of Immunology, 147: 1037–1044, No. 3, (Aug. 1, 1991).
Howard et al., Immunogenetics 33: 74–76 (1991).
Krummel et al., J. Exp. Med. 182: 459–465 (Aug. 1995).
Lane et al., J. Exp. Med. 179: 819–830 (Mar. 1994).
Linsley et al., Immunity 1: 793–801 (Dec. 1994).
Linsley et al., J. Exp. Med. 173: 721–730 (Mar. 1991).
Marengère et al., Science 272: 1170–1173 (24 May 1996).
Ronchese et al., J. Exp. Med. 179: 809–817 (Mar. 1994).
Tivol et al., Immunity 3: 541–547 (Nov. 1995).
Walunas et al., Immunity 1: 405–413 (Aug. 1994).
Waterhouse et al., Science 270: 985–988 (10 Nov. 1995).
Case et al., The Journal of Biological Chemistry 269, No. 14: 10467–10474, (Issue of Apr. 8, 1994).

Feng et al., Science 259: 1607–1611 (12 Mar. 1993).
Klinghoffer et al., The Journal of Biological Chemistry 270, No. 38: 22208–22217 (Issue of Sep. 22, 1995).
Pelicci et al., Cell 70:93–104 (10 Jul. 1992).
Seely et al., The Journal of Biological Chemistry 270, No. 32: 19151–19157 (Issue of Aug. 11, 1995).
Tauchi et al., The Journal of Biological Chemistry 270, No. 10: 5631–5635 (Issue of Mar.10, 1995).
Tauchi et al., The Journal of Biological Chemistry 269, No. 40: 25206–25211 (Issue of Oct. 7, 1994).
Tomic et al., The Journal of Biological Chemistry 270, No. 36: 21277–21284 (Issue of Sep. 8, 1995).
Yamauchi et al., The Journal of Biological Chemistry 270, No. 25: 14871–14874 (Issue of Jun. 23, 1995).
Doody et al., Science 269: 242–244 (14 Jul. 1995).
Law et al., J. Exp. Med. 183: 547–560 (Feb. 1996).
Pleiman et al., Immunology Today 15, No. 9: 393–399 (1994).
Freeman et al., Cloning of B7–2: a CTLA–4 counter-receptor that costimulates human T cell proliferation, Science, 626: 909–911, Nov. 1993.
Lindsten et al., Characterization of CTLA-4 structure and expression on human T cells, J. Immunol., 151(7): 3489–3499, Oct. 1993.
Linsley et al., The role of the CD28 receptor during T cell responses to antigen, Annu. Rev. Immunol., 11:191–212, 1993.
Linsley et al., Distinct roles for CD28 and cytotoxic T lymphocyte–associated molecule–4 receptors during T cell activation?, J. Exp. Med., 182: 289–292, Aug. 1995.
Linsley et al., Lymphocyte activation: T–cell regulation by CTLA–4, Curr. Biol., 6(4): 398–400, 1996.
Schneider et al., CTLA–4 binding to the lipid kinase phosphatidylinositol 3–kinase in T cells, J. Exp. Med., 181: 351–355, Jan. 1995.
Sugimoto et al., Expression, purification, and characterization of SH2–containing protein tyrosine phosphatase, SH–PTP2, J. Biol. Chem., 268 (30): 22771–22776, Oct. 1993.

*Primary Examiner*—Stephen Walsh
*Assistant Examiner*—Claire M. Kaufman
*Attorney, Agent, or Firm*—Nancy A. Oleski; Ron K. Levy; Steven M. Odre

[57] ABSTRACT

Disclosed are methods for identifying a molecule that inhibits SYP activity in a T-cell.

14 Claims, 10 Drawing Sheets

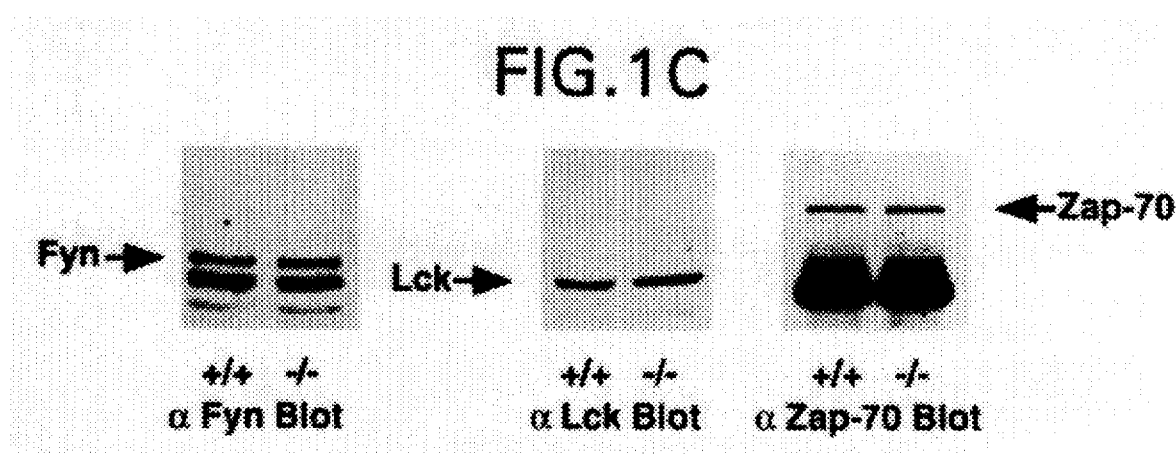

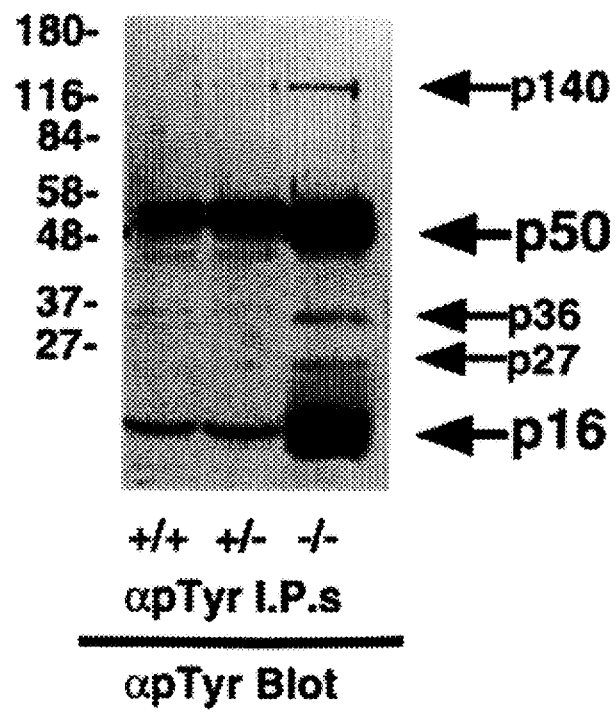
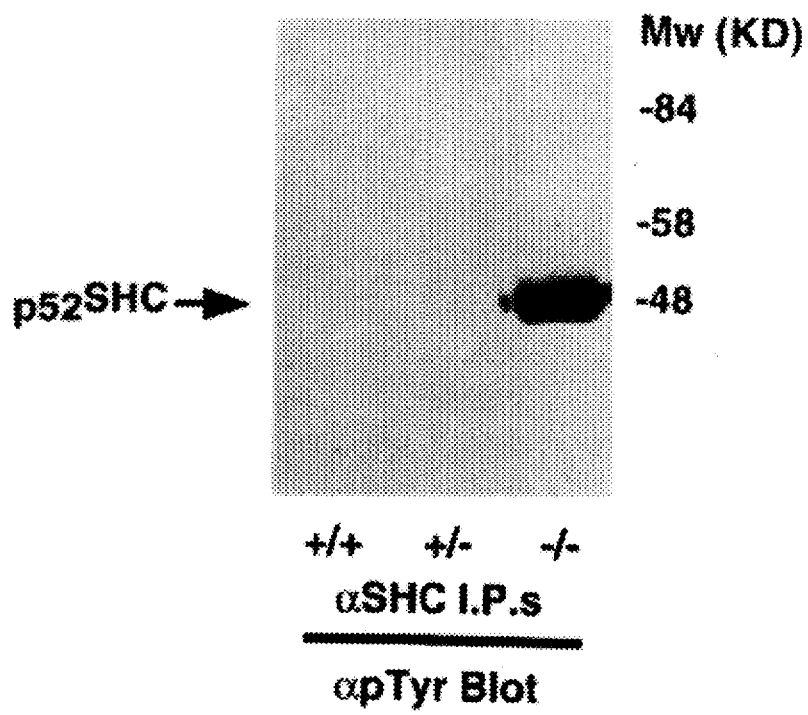

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:1:

```
Lys Met Leu Lys Lys Arg Ser Pro Leu Thr Thr Gly Val Tyr Val Lys
1               5                   10                  15
Met Pro Pro Thr Glu Pro Glu Cys Glu Lys Gln Phe Gln Pro Tyr Phe
                20              25                  30
Ile Pro Ile Asn
        35
```

( 2 ) INFORMATION FOR SEQ ID NO:2:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Lys Gln Phe Gln Pro Tyr Phe Ile Pro Ile Asn
1               5                   10
```

( 2 ) INFORMATION FOR SEQ ID NO:3:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:3:

```
Tyr Val Lys Met
1
```

( 2 ) INFORMATION FOR SEQ ID NO:4:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:4:

```
Tyr Phe Ile Pro
1
```

METHODS OF INHIBITING SYP BINDING TO A CTLA-4 RECEPTOR

FIELD OF THE INVENTION

This invention relates to methods for modulating the negative regulation of T-cell activation. More specifically, the invention concerns methods to identify a molecule that inhibits SYP dephosphorylation activity of p52SHC in T-cells when SYP is complexed with the CTLA-4 receptor.

BACKGROUND OF THE INVENTION

T-cells are a class of white blood cells that are responsible for the cell-mediated immune response to many types of antigens encountered by the immune system.

Cytolytic (cytotoxic) T-lymphocyte-associated antigen number 4 receptor ("CTLA-4 receptor"; also referred to herein as "CTLA-4") is a protein that is expressed on the surface of T-cells after these cells are "activated", i.e., exposed to an antigen which serves to stimulate them (Green et al., *Immunity*, 1:501 [1994]; Wallunas et al., ibid., p.405). The cDNA encoding mouse CTLA-4 receptor has been cloned and sequenced (Brunet et al., *Nature*, 328: 267 [1987]). In mice, CTLA-4 cDNA has approximately 76 percent homology with another T-cell surface receptor protein called CD28, and the two genes are located in close proximity to each other on mouse chromosome 1 (Harper et al., *J. Immunol*, 147: 1037 [1991]; Howard et al., *Immunogenet.*, 33: 74 [1991]). Both CTLA-4 receptor and CD28 bind to the protein ligands B7-1 and B7-2 (Linsley et al., *Immunity*, 1: 793 [1994]; Linsley et al., *J. Exp. Med.*, 173: 721 [1991]); B7-1 and B7-2 are expressed on the surface of immune system cells known as antigen presenting cells (APCs). Due to its similarity to CD28, the CTLA-4 receptor has been postulated to play a role in T-cell activation.

Various studies have been conducted in an attempt to identify the precise role of CTLA-4 receptor in immune system function.

Gribben et al. (*Proc. Natl. Acad. Sci. USA*, 92: 811–815 [1995]) describe studies wherein cross-linking of the CTLA-4 receptor on previously activated T-cells can purportedly mediate apoptosis (cell death) of these cells.

Krummel et al. (*J. Exp. Med.*, 182:459[1995]) describe the use of anti CTLA-4 receptor monoclonal antibodies and CTLA-4 receptor-Ig fusion proteins that have been used to assess the expression pattern of CTLA-4 receptor.

Ronchese et al. (*J. Exp. Med.*, 179: 809–817 [1994]) describe a mouse containing a transgene encoding a soluble form of CTLA-4 receptor. The mouse is purportedly defective in T-cell dependent antibody production.

Lane et al. (*J. Exp. Med.*, 179: 819–830 [1994]) describe a transgenic mouse purportedly expressing a soluble form of CTLA-4 receptor.

Waterhouse et al., (*Science*, 270:985–988 [1995]) describe a mouse in which the gene encoding CTLA-4 is not expressed. The T-cells of mice with this gene disruption show constitutive activation of T-cells, and the mice have an early lethality.

Phosphatases are known to be involved in the cell signaling pathways in many types of cells, including, inter alia, T-cells. The phosphotyrosine phosphatase SYP (also called SHPTP2, PTP1D, and PTP2C) is an intracellular phosphatase found in T-cells as well as a variety of other types of cells. SYP contains two SH2 (src homology 2) domains near the amino terminus of the molecule, as well as a phosphotyrosine phosphatase domain near the carboxy terminus of the molecule (Feng et al., *Science*, 259:1604 [1993]). SYP has been shown to associate with certain cell membrane bound receptors such as activated EGFR (Tomic et al., *J. Biol. Chem.*, 270:21277–21284 [1995]; Yamauchi et al., *J. Biol. Chem.*, 270:14871–14874 [1995]), PDGFR (Klinghoffer et al., *J. Biol. Chem.*, 270:22208–22217 [1995]), IGF-1 receptor (Seely et al., *J. Biol. Chem.*, 270:19151–19157 [1995]), c-kit receptor (Tauchi et al., *J. Biol. Chem.*, 269:25206–25211 [1994]), and EPOR (Tauchi et al., *J. Biol. Chem.*, 270:5631–5635 [1995]). See also Case et al. (*J. Biol. Chem.*, 269:10467–10474 [1994]).

Another intracellular signaling protein found in T-cells and other cells is SHC. SHC contains a SH2 domain near the carboxy terminus of the molecule. Three known isoforms of SHC are p66SHC, p52SHC and p46SHC, which encode polypeptides of approximately 66 kD, 52 kD and 46 kD, respectively (see Pelicci et al., *Cell*, 70:93–104 [1992]). In T-cells, p52SHC appears to be involved in the signal transduction pathway that ultimately modulates ras activity.

Many cell signaling strategies are conserved between B and T cell antigen receptors. B-cell receptor activation results in the phosphorylation of CD22 which then binds the SH2-containing tyrosine phosphatase SHP (Pleinman et al., *Immunol. Today*, 15:393 [1994]; Doody et al., *Science*, 269:242 [1995]; Law, C-L, *J. Exp. Med.*, 183:547 [1996]). Therefore, the inventors herein investigated whether the T-cell receptor CTLA-4 could associate with an intracellular protein tyrosine phosphatase, and, in particular, a SH-2 domain containing protein tyrosine phosphatase. The results, discussed infra, show that CTLA-4 does in fact associate with the protein tyrosine phosphatase SYP.

In view of the importance of T-cell function in the immune system, there is a need in the art to provide assays for screening drugs useful in specifically modulating T-cell activation.

Accordingly, it is an object of the present invention to provide a method of identifying a molecule that can modulate T-cell activation.

This and other such objects will readily be apparent to one of ordinary skill in the art.

SUMMARY OF THE INVENTION

In one embodiment, the present invention provides a method of identifying a molecule that inhibits SYP activity in a T-cell comprising contacting the molecule with SYP in the presence of phosphorylated CTLA4 receptor, and assaying for SYP binding to phosphorylated CTLA4 receptor.

In another embodiment, the molecule is an inorganic molecule, or the molecule is an organic molecule that is naturally occurring or produced synthetically.

In yet another embodiment, the assay to test the molecule is conducted in vitro.

In still another embodiment, the assay to test the molecule is conducted in vivo.

In another embodiment, the present invention provides a method of identifying a molecule that inhibits SYP activity in a Tcell comprising contacting the molecule with SYP in the presence of phosphorylated CTLA4 receptor and phosphorylated p52SHC, and assaying for dephosphorylation of p52SHC.

BRIEF DESCRIPTION OF THE DRAWINGS

FIGS. 1B–1C depict Western blots of immunoprecipitates that were separated by SDS-PAGE. FIG. 1B shows an anti-Zap-70 immunoprecipitate which was Western blotted and probed with an anti-phosphotyrosine antibody. FIG. 1C shows three Western blots probed with the indicated antibodies.

FIGS. 2A–2G depict a series of Western blots. "MW" refers to molecular weight; "+/+, +/−, and −/−" refer to T-cells from wild type, heterozygous CTLA-4 receptor deficient, and homozygous CTLA-4 receptor deficient mice; "I.P.s" refers to immunoprecipitates, and the abbreviation in front of I.P.s refers to the antibody used for immunoprecipitation; the abbreviation in front of the word "blot" refers to the antibody used to probe each Western blot. Lanes 1–4 in FIG. 2G correspond to anti-CD3ζ immunoprecipitate from CTLA-4 receptor wild type (Lane 1) and knockout (Lane 2) T cells, and anti-p52SHC immunoprecipitate from CTLA-4 receptor wild type (Lane 3) and knockout (Lane 4) T-cells.

DETAILED DESCRIPTION OF THE INVENTION

Figure 1A:
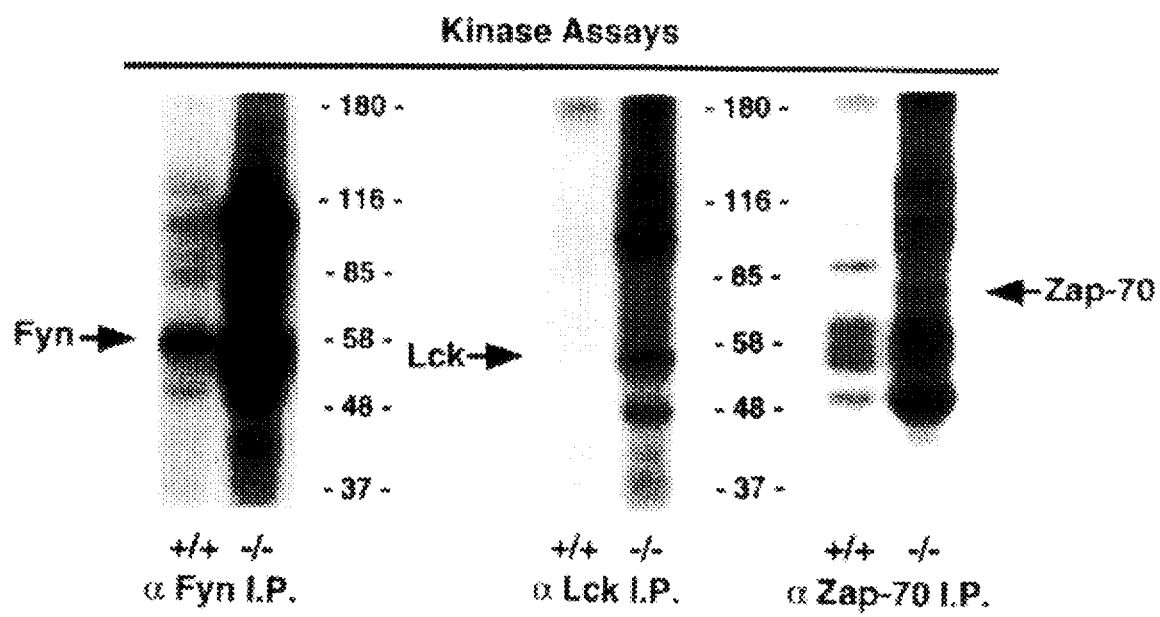
FIG. 1A depicts three SDS electrophoresis gels in which immunoprecipitated proteins were treated with a kinase reaction (see Example I). The numbers on the right side of each gel refer to molecular weights; "I.P." refers to immunoprecipitation with the antibody indicated; "+/+ and −/−" refer to T-cells from wild type and homozygous CTLA-4 receptor deficient mice.

This invention contemplates a method of identifying a molecule or molecules that decreases) or inhibit(s) SYP activity in a T-cell. The method for identification of such a molecule comprises in vitro and/or in vivo assays designed to detect either CTLA-4 receptor interaction with SYP or SYP dephosphorylation of p52SHC in T-cells.

As used herein, the term "molecule" is meant to include both organic and inorganic compounds. An organic molecule may include, without limitation, a naturally occurring or chemically synthesized molecule, and/or a molecule produced by recombinant DNA technology.

The phrase "SYP activity in a T-cell" as used herein means dephosphorylation of p52SHC by SYP when SYP is complexed with a T-cell CTLA-4 receptor.

Assays to identify a molecule that decreases or inhibits SYP activity can be conducted either in vivo or in vitro; in vitro assays can be conducted using either cultured T-cells or spleen cells, or other appropriate cell lines, or purified proteins.

Purified proteins can be used for in vitro assays termed "binding assays" herein. Such assays are described below.

Typically, the in vitro binding assays will require the use of purified CTLA-4 receptor protein, purified SYP protein, and, for some assays, purified p52SHC protein. These proteins may be prepared using a variety of techniques, as for example, isolation and purification of each naturally occurring protein from T-cells or other cells that naturally express the proteins; chemical synthesis of the proteins; or preparation of the DNA encoding each protein and expression of this DNA in a suitable host cell.

Preparation of either cDNA or genomic DNA or biologically active fragments thereof encoding CTLA-4 receptor, SYP, or p52SHC may be accomplished using chemical synthesis techniques such as those set forth by Engels et al. (Angew. Chem. Intl. Ed. Engl., 28:716–734 [1989]). These methods include, inter alia, phosphotriester, phosphoamidite, and H-phosphonate techniques. Alternatively, the cDNA or genomic DNA may be isolated from T-cells of human or other origin, or from other cell sources (human or non-human), using well known molecular biology techniques such as those set forth by Sambrook et al. (Molecular Cloning: A Laboratory Manual, Cold Spring Harbor Laboratory Press, Cold Spring Harbor, N.Y.) or by Ausubel et al. (Current Protocols in Molecular Biology, John Wiley & Sons, N.Y. [1995]).

In some cases, it may be desirable to obtain only a portion of the full length cDNA or genomic DNA of the protein, i.e., a DNA fragment, as, for example, where it is preferred to prepare a fusion protein or to use a truncated protein in the binding assays. For example, the cytoplasmic tail of the CTLA-4 receptor contains two potential sites for tyrosine phosphorylation, e.g., Tyr201-Val-Lys-Met, and Tyr218-Phe-Ile-Pro. A truncated CTLA-4 receptor molecule containing one or both of these regions could be prepared using PCR or another suitable method, and this truncated molecule could be used in the binding assays described below. In addition, a truncated version of SYP comprising the two SH2 domains can be used in those binding assays designed to evaluate CTLA-4 receptor/SYP interaction. Similarly, for those assays in which p52SHC is used, a truncated version of p52SHC containing the phosphorylation site which SYP is active against can be prepared and used instead of the full length molecule in the appropriate binding assays.

Fragments of cDNA or genomic DNA encoding the desired portions of each protein can be prepared by a variety of methods such as, for example, restriction endonuclease digestion of the full length DNA followed by agarose gel isolation; PCR amplification of the desired fragment of the DNA using primers that hybridize to each end of the region of the protein to be amplified; and the like.

Whether full length or truncated DNAs of each protein are to be used in the binding assays, the cDNA or genomic DNA encoding each molecule or fragment thereof can be inserted into a suitable vector, i.e., one which is compatible with the host cell to be used to express the DNA.

Preferred vectors for practicing this invention are those which are compatible with bacterial, insect, or mammalian host cells. Such vectors include, inter alia, pCRII (Invitrogen Company, San Diego, Calif.), pBSII (Stratagene Company, LaJolla, Calif.), and pETL (BlueBacII; Invitrogen), or pCFM1656 (see U.S. Pat. No. 5,470,719, issued Nov. 28, 1995) Insertion of the selected DNA into the vector may readily be accomplished using standard molecular cloning methods well known on the art, i.e., restriction endonuclease digestion and ligation methods.

Host cells used for CTLA4 receptor, SYP, or p52SHC DNA expression may be prokaryotic (such as E. coli) or eukaryotic (such as a yeast cell, an insect cell, or a vertebrate cell) in origin. The host cell, when cultured under appropriate conditions, can express the protein encoded by the foreign DNA on the vector. This protein can subsequently be collected from the culture medium (if the host cell secretes it into the medium) or directly from the host cell producing it (if it is not secreted). After collection, the protein can be purified using methods such as molecular sieve chromatography, affinity chromatography, HPLC, and the like.

Selection of the host cell will depend in part on whether the CTLA-4 receptor, SYP, or p52SHC protein is to be glycosylated, phosphorylated or otherwise posttranslationally modified (in which case eukaryotic host cells are preferred), and the manner in which the host cell is able to "fold" the protein into its native tertiary structure (e.g., proper orientation of disulfide bonds, etc.) such that biologically active protein is prepared by the cell. However, where the host cell is not able to synthesize biologically active protein, the protein may be "folded" after synthesis using appropriate chemical conditions as discussed below.

Cells or cell lines that may be suitable for use herein are mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines include the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for preparing certain proteins are bacterial cells. For example, the various strains of *E. coli* (e.g., HB101, DH5α, DH10, and MC1061) are commonly used as host cells for expression of foreign DNA. Various strains of *B. subtilis*, Pseudomonas spp., other Bacillus spp., Streptomyces spp., and the like may also be employed in this method.

Many strains of yeast cells known to those skilled in the art are also available as host cells for expression of the polypeptides of the present invention. Additionally, where appropriate, insect cells may be utilized as host cells for protein production (See Miller et al., *Genetic Engineering* 8: 277-298 [1986]).

Insertion (also referred to as "transformation" or "transfection") of the vector into the selected host cell may be accomplished using such methods as calcium chloride treatment, electroporation, microinjection, lipofection or DEAE-dextran treatment. The method selected will in part be a function of the type of host cell to be used. These methods and other suitable methods are well known to the skilled artisan, and are set forth, for example, in Sambrook et al., (*Molecular Cloning: A Laboratory Manual*, Cold Spring Harbor Laboratory Press, Cold Spring Harbor, N.Y. [1989]).

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of CTLA-4 receptor, SYP, or p52SHC protein produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or bio-activity assays such as phosphorylation or dephosphorylation (either autophosphorylation, or with respect to another cellular substrate or a synthetic substrate such as O-nitro-phenyl phosphate), T-cell signaling and/or activation/deactivation, or the like.

If the CTLA-4 receptor, SYP, or p52SHC polypeptide has been designed to be secreted from the host cells (i.e. where a signal sequence is attached to the DNA encoding the protein), the majority of polypeptide will likely be found in the cell culture medium. If however, the CTLA-4 receptor, SYP, or p52SHC protein is not secreted from the host cells, it will primarily be present in the cytoplasm (for eukaryotic, gram positive bacteria, and insect host cells) or in the periplasm (for gram negative bacteria host cells) of the host cell.

For purification of cytoplasmic protein, the host cells are typically first disrupted mechanically or osmotically to release the cytoplasmic contents into a buffered solution. The protein can then be isolated from this solution.

Purification of CTLA-4 receptor, SYP, or p52SHC polypeptide from a cytoplasmic solution or from the culture medium can be accomplished using a variety of techniques. If the polypeptide has been synthesized such that it contains a tag such as Hexahistidine or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing CTLA-4 receptor, SYP, or p52SHC). For example, polyhistidine binds with great affinity and specificity to nickel, thus an affinity column of nickel (such as the Qiagen nickel columns) can be used for purification of CTLA-4 receptor, SYP, or p52SHC which is linked to polyHis. (See for example, Ausubel et al., eds., *Current Protocols in Molecular Biology*, Section 10.11.8, John Wiley & Sons, New York [1993]).

Where the protein is synthesized without a tag, other well known procedures for purification from solution can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the protein expressed in bacterial host cells will be found primarily in the periplasmic space of the bacteria, the contents of the periplasm, i.e., the inclusion bodies (for gram-negative bacteria) can be extracted from the host cell using any standard technique known to the skilled artisan. For example, the host cells can be lysed to release the contents of the periplasm by French press, homogenization, and/or sonication. The homogenate can then be centrifuged.

The inclusion bodies can often bind to the inner and/or outer cellular membranes of the bacteria, and thus will be found primarily in the pellet material after centrifugation. The pellet material can then be treated with a chaotropic agent such as guanidine or urea to release, break apart, and solubilize the inclusion bodies. The protein in its now soluble form can then be analyzed using gel electrophoresis, immunoprecipitation or the like, and purified using standard methods such as those set forth below and in Marston et al. (*Meth. Enz.*, 182:264-275 [1990]).

Partial or complete purification of the CTLA-4 receptor, SYP, or p52SHC protein in solution can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying CTLA-4 receptor, SYP, or p52SHC protein or biologically active fragments thereof using recombinant DNA techniques, these proteins, fragments, and/or derivatives thereof, may be prepared by chemical synthesis methods (such as solid phase peptide synthesis) using methods known in the art such as those set forth by Merrifield et al., (*J. Am. Chem. Soc.*, 85:2149 [1964]), Houghten et al. (*Proc Natl Acad. Sci. USA*, 82:5132 [1985]), and Stewart and Young (Solid Phase Peptide Synthesis, Pierce Chem Co, Rockford, Ill. [1984]). Chemically synthesized CTLA-4 receptor, SYP, or p52SHC proteins or fragments thereof may be oxidized using methods set forth in these references to form disulfide bonds.

As discussed in the Examples below, both p52SHC and CTLA-4 receptor require phosphorylation of certain tyrosine residues to be active. Phosphorylation of these residues may be accomplished in a variety of ways. If the proteins have been purified directly from cells that naturally express them, the proteins may already be phosphorylated. If the proteins are prepared using recombinant DNA technology procedures, they may be automatically phosphorylated if synthesized in certain mammalian host cells. Where the proteins are not naturally phosphorylated, it is possible to synthetically phosphorylate them. Suitable procedures for such synthetic phosphorylation are set forth below.

An alternative to using recombinantly prepared or chemically synthesized proteins in the binding assays is to use naturally occurring proteins. To purify such naturally occurring CTLA-4 receptor protein, naturally occurring SYP protein, and/or naturally occurring p52SHC protein directly from T-cells or other cells that express these proteins, the cells can be obtained from the mammal of choice (preferably human) for example, by purifying the T-cells using T-cell enrichment columns (R&D Systems, catalog no. MTCC-1000, Minneapolis, Minn.). CTLA-4 receptor protein can be purified from the cell using methods known in the art for membrane bound proteins such as detergent solubilization or exposure to a chaotropic agent, followed by HPLC, affinity chromatography, molecular sieve chromatography, native or SDS gel electrophoresis and electroelution, immunoprecipitation, and/or other such methods well known in the art. If the purified protein is inactive, activity may be restored by protein refolding (i.e., controlled removal of detergent and/or the use of a chaotropic agent from the purified protein by dialysis).

Purification of naturally occurring SYP and p52SHC, both of which are cytoplasmic proteins, can be accomplished by first lysing the cells with a detergent or a chaotropic compound, followed by one or more standard protein purification procedures as set forth above.

Once the proteins have been purified using one or more procedures as set forth above, both CTLA-4 receptor and p52SHC must be phosphorylated for the in vitro assays. As mentioned above, in some cases, these proteins may be phosphorylated when synthesized, i.e., where the naturally occurring proteins are purified from T-cells or other appropriate cells, or where the DNA encoding these proteins is expressed in certain host cells that are capable of phosphorylating the proteins. In situations where CTLA-4 receptor and/or p52SHC are not phosphorylated, it is possible to phosphorylate them by adding ATP, a protein tyrosine kinase (such as p56lck, p55fyn, or zap70, Life Technologies, Grand Island, N.Y.), and a suitable buffer (usually containing manganese or magnesium) to the protein.

In Vitro Assays

For ease of reading, the following definitions are used herein for describing the assays:

"Test molecule(s)" refers to the molecule(s) that is under evaluation as an inhibitor of SYP, either by virtue of its potential ability to block the interaction of SYP with CTLA-4 receptor, or by virtue of its potential ability to block the dephosphorylation activity of SYP against p52SHC.

A. In Vitro Assays Using Purified Proteins

Several types of in vitro assays using purified proteins may be conducted to identify a molecule that disrupts SYP activity in a T-cell. Such disruption may be accomplished by a molecule that either inhibits CTLA-4 receptor/SYP complex formation, or by a molecule that inhibits SYP dephosphorylation of p52SHC when SYP is complexed with CTLA-4 receptor.

In one type of assay, CTLA-4 receptor protein can be immobilized by attachment to the bottom of the wells of a microtiter plate. Radiolabeled SYP (for example, iodinated SYP) and the test molecule(s) can then be added either one at a time (in either order) or simultaneously to the wells. After incubation, the wells can be washed and counted using a scintillation counter for radioactivity to determine how much (if any) of the SYP protein has been able to complex with CTLA-4 receptor in the presence of the test molecule. Typically, the molecule will be tested over a range of concentrations, and a series of control "wells" lacking one or more elements of the test assays can be used for accuracy in evaluation of the results. An alternative to this method involves reversing the "positions" of the proteins, i.e., immobilizing SYP to the mictrotiter plate wells, incubating with the test molecule and radiolabeled CTLA-4 receptor, and then washing the wells; the amount of CTLA-4 receptor that binds can then be assessed by counting the radioactivity in each well (see, for example, chapter 18 of *Current Protocols in Molecular Biology*, Ausubel et al., eds., John Wiley & Sons, New York, N.Y. [1995] for protein phosphorylation analysis techniques).

Several means other than radiolabelling are available to "mark" the SYP or CTLA-4 receptor protein to quantify the binding between these proteins. For example, direct conjugation of the protein to biotin (the presence of SYP-biotin or CTLA-4-biotin can then be detected using streptavidin linked to an enzyme, such as horse radish peroxidase [HRP] or alkaline phosphatase [AP], that can be detected colorometrically, or fluorescent tagging of streptavidin), or by an antibody directed to SYP or CTLA-4 receptor that is conjugated to biotin (which can be detected with enzyme-linked streptavidin linked to AP or HRP after incubation).

An alternative to microtiter plate type of binding assays comprises immobilizing either SYP or CTLA-4 receptor protein to agarose beads, acrylic beads or other types of such inert substrates. The substrate-protein complex can be placed in a solution containing the complementary protein and the test molecule; after incubation, the beads can be precipitated by centrifugation, and the amount of binding between SYP and CTLA-4 receptor can be assessed using the methods described above. Alternatively, the substrate-protein complex can be immobilized in a column and the test molecule and complementary protein passed over the column. Formation of the CTLA4 receptor/SYP complex can then be assessed using any of the techniques set forth above, i.e., radiolabeling, antibody binding, or the like.

Another type of in vitro assay that is useful for identifying a molecule to inhibit SYP activity is the Biacore assay system (Pharmacia, Piscataway, N.J.) using a surface plasmon resonance detector system and following the manufacturer's protocol. This assay essentially involves covalent binding of either SYP or CTLA-4 receptor protein to a dextran-coated sensor chip which is located in a detector. The test molecule and the other complementary protein can then be injected into the chamber containing the sensor chip either simultaneously or sequentially and the amount of complementary protein that binds can be assessed based on the change in molecular mass which is physically associated with the dextran-coated side of the of the sensor chip; the change in molecular mass can be measured by the detector system.

In some cases, it may be desirable to evaluate two or more test molecules together for use in decreasing or inhibiting SYP activity. In these cases, the assays set forth above can be readily modified by adding such additional test molecule (s) either simultaneously with, or subsequently to, the first test molecule. The remainder of steps in the assay are as set forth above.

An alternative means to inhibit the activity of SYP is to identify a molecule or molecules that prevent SYP dephosphorylation activity of p52SHC in T-cells, when CTLA-4 receptor protein is complexed with SYP protein. Assays to test such molecules are analogous to the assays set forth above, except that the proteins used in the assays are SYP, CTLA-4 receptor, and p52SHC. The assessment of whether the test molecule is effective in blocking SYP activity can be measured by the degree to which p52SHC is dephosphorylated in the presence of the test molecule.

In one type of assay, the wells of microtiter plates can be coated with p52SHC protein that has been phosphorylated using radiolabeled phosphorus (e.g., 32P-ATP for the enzymatic phosphorylation procedure). The test molecule, SYP, and CTLA-4 receptor can then be added either simultaneously or individually over time. After a period of incubation, the wells can be washed and counted for radiolabeled phosphorus. The amount of radiolabel in the well is proportional to the amount of SYP dephosphorylation activity of p52SHC.

The Biacore assay system described above can also be used as a means to measure dephosphorylation activity of SYP in response to the presence of a test molecule. Here, p52SHC can be covalently bound to the sensor chip; the test molecule and the SYP/CTLA-4 receptor complex can then be added either individually over time or simultaneously. After incubation and washing the chip, the amount of dephosphorylation of p52SHC can be evaluated by adding an anti-phosphotyrosine antibody to the chip; the amount of antibody that binds will be a function of the amount of dephosphorylation of p52SHC that occurred, and antibody binding can be detected by the Biacore sensor due to a change in molecular mass of the detector chip. Alternatively, an anti-p52SHC antibody or an antitag antibody (where p52SHC is fused to an epitope tag) can be covalently linked to the sensor chip; p52SHC can then bind to the antibody and the change in molecular mass can be detected as described.

B. In Vitro Assays Using Cultured Cells

Cell cultures of T-cells or other types of cells in which p52SHC is dephosphorylated by SYP when SYP is complexed to CTLA-4 receptor can be used to evaluate test molecules for SYP inhibition. The T-cells can be obtained from any mammal, but preferably will be from human or other primate, canine, or rodent sources. The T-cells can readily be separated from other types of cells using T-cell enrichment columns (R and D Systems) and following the manufacturer's protocol.

In one type of cell culture assay, T-cells can first be "activated" by (1) incubating them with a substance that stimulates T-cell proliferation such as ConcanavalinA (ConA) or phytohemaglutinin (PHA) or phorbol myristate acid ester (PMA) plus a calcium ionophore, or (2) incubating the cells with an anti-TCR (T-cell receptor) antibody or an anti-CD3 antibody. Incubation is typically conducted for a period of 1–5 days after which the cells can be washed and the test molecule can be added for a period of time. After washing the cells to remove any residual test molecule, the amount of phosphorylation of p52SHC can be determined by isolating the p52SHC from the cells (as, for example, by immunoaffinity chromatography or other procedures set forth above) and incubating the purified p52SHC with an anti-phosphotyrosine antibody. The amount of antibody that binds can be detected by a variety of methods such as a second antibody linked to HRP, AP, or a fluorescent tag, where this second antibody recognizes and binds to the first antibody.

In another type of cell culture assay, the activated T-cells can be incubated with the test molecule and 3H-thymidine. After a period of time, cell proliferation can be assessed by counting the cells for radioactivity, and/or by mechanically counting the number of cells In Vivo Assays In vivo assays to evaluate a test molecule can be conducted using any type of mammal such as a mouse, rat, rabbit, dog, cat, monkey or other primate such as a human. For these assays, the mammal can first be exposed to an antigen such as a virus (e.g., LCMV for mice) that will serve to activate T-cells. The test molecule can subsequently be administered by injection or other suitable means (oral administration, catheter, or the like). After a suitable period which allows for antibody production in response to the antigen, assays for IgG and/or IgM titers, as well as T-cell count, and/or IL-2 production can be run to assess T-cell activation.

The methods of the present invention are useful for identifying a molecule or molecules, which, by altering SYP activity, can serve to modulate T-cell activation through CTLA-4 receptor. Such molecules can find use in suppressing T-cell activity, as, for example, in autoimmune diseases such as rheumatoid arthritis, lupus, organ rejection, and other such disorders wherein negative regulation of T-cell proliferation goes unchecked in the patient. In certain other situations, it may be desirable to identify a molecule that serves to increase or maintain T-cell activation (i.e., AIDS or tumor proliferation) in order to enhance the immune response.

The following Examples are meant to illustrate certain embodiments of the invention, and should not be construed as limiting the scope of the invention in any way.

EXAMPLES

Example I fyn, lck, and Zap-70 Constitutive Expression in T-Cells Lacking CTLA-4 Expression About 20 million T-cells from wild type and CTLA-4 homozygous knockout mice (Waterhouse et al., supra) were obtained by removing the spleen and lymph nodes from the mice and passing them through a fine-wire mesh to make a cell suspension. The cells were washed in PBS, and then lysed in TNE buffer (50 mM Tris pH 8.0, 1 percent NP-40 detergent, 20 mM EDTA pH 8.0, 10 µg/ml Leupeptin, 10 µg/ml Aprotinin, 1 mM PMSF, and 1 mM sodium vanadate). The cell lysates were divided into aliquots, and the protein concentration was standardized for each aliquot. Each aliquot (controls excepted) was then incubated with one of three rabbit polyclonal antibodies (all obtained from Santa Cruz Laboratories, Santa Cruz, Calif.): anti-fyn, anti-lck, or anti-Zap-70. The incubation conditions were 1 hour at 4° C. After incubation, the immunoprecipitates were washed three times in TNE buffer and twice in kinase buffer (50 mM Tris-HCl, pH 7.0, 8 mM magnesium chloride, 2 mM manganese chloride, 1 mM DTT). After washing, an aliquot of each immunoprecipitate was incubated with 40 µl kinase buffer and 1 µl of 32P-ATP (Amersham) at 37° C. for about 10 minutes. The kinase reaction was stopped by the addition of 40 µl of 2×Lammeli buffer (100 mM tris-HCl, pH 6.8, 20 percent beta-mercaptoethanol, 4 percent SDS, 0.2 percent Bromophenol blue, and 20 percent glycerol), and an aliquot of each sample was then exposed to SDS-PAGE. The gel was dried and exposed with Kodak-XAR film for about one hour.

Separately, an aliquot of each immunoprecipitate was separated by SDS-PAGE, transferred to nitrocellulose paper, and Western blotted using standard methods. Each blot was incubated with a first antibody that was either antiphosphotyrosine antibody (FIG. 1C; antibody clone 4G10 obtained from Upstate Biotech Institute, Lake Placid, N.Y.) which detects phosphotyrosine residues, anti-fyn, anti-lck, or anti-Zap-70. The blots were incubated for about 1 hour at 37° C. and then washed using standard methods. The first antibody was then detected using either HRP-donkey anti rabbit or HRP-goat anti mouse polyclonal antiserum. HRP was detected using the enhanced chemiluminescence technique ("ECL", Amersham, Arlington Heights, Ill.) and following the manufacturer's protocol.

The results of SDS-PAGE after the kinase reaction are shown in FIG. 1A. As can be seen, there was very little phosphorylation of the immunoprecipitated proteins in the wild type cells, although a band is apparent in the fyn immunoprecipitate. In the CTLA-4 knockout cells, significantly more phosphorylation was apparent for all immunoprecipitates.

Figure 1B:
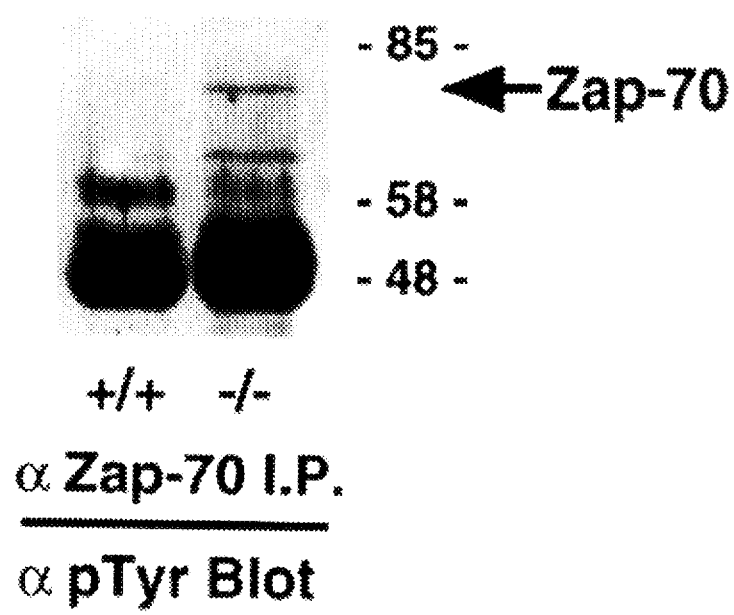

The results of Western immunoblotting of the Zap-70 immunoprecipitate ("I.P.") are shown in FIG. 1B. As can be seen in FIG. 1B, antiphosphotyrosine antibodies detected more tyrosine phosphorylation in Zap-70 immunoprecipitates from CTLA-4 knockout cells than from wild type cells. FIG. 1C shows a series of "control" Western blots of the various immunoprecipitates, each of which was probed with the indicated antibody which corresponds to the antibody used for the immunoprecipitation.

Example II

Identification of CTLA-4/SYP Association

To assess the membrane and intracellular components involved in the constitutive activation of T-cells, T-cells were isolated from a CTLA-4 receptor deficient mouse (Waterhouse et al., Science, 270:985 [1995]; Tivol et al., Immunity, 3:541 [1995]) as well as from a wild type mouse and a mouse heterozygous for CTLA-4 receptor expression. The T-cells from each type of mouse were isolated by removing the spleen and lymph nodes, passing them through a fine-wire mesh to make a cell suspension, washing in PBS, and then adding TNE buffer (50 mM Tris pH 8.0, 1 percent NP-40 detergent, 20 mM EDTA pH 8.0, 10 µg/ml Leupeptin, 10 µg/ml Aprotinin, 1 mM PMSF, and 1 mM sodium vanadate) to lyse the cells. About 10 million cells were added to about 1 ml of this buffer. Lysate was prepared by incubating the cells and buffer, and then centrifuging the cells and collecting the supernatant. The protein concentration of each lysate was standardized, and equal amounts of protein were incubated with about 2–10 µg of either mouse monoclonal anti-phosphotyrosine antibodies (clone 4G10, Upstate Biotech Institute, Lake Placid, N.Y.), rabbit polyclonal anti-p52SHC antibodies (Signal Transduction Laboratories, Lexington, Ky.), mouse monoclonal anti CD3ζ antibodies (Signal Transduction Laboratories), or rabbit polyclonal anti-Grb2 antibodies (Signal Transduction Laboratories). The immune complexes were immunoprecipitated using a second antibody (either hamster anti-mouse, or goat-anti-rabbit) linked to Sepharose beads. After immunoprecipitation, the components were separated by SDS gel electrophoresis, and transferred to nitrocellulose paper. The Western blots were then probed with the first antibody as indicated in FIGS. 2A–2G. Incubation conditions were: room temperature for about one hour, followed by three washes in PBS containing 0.05 percent NP-40 (Sigma, St. Louis, Mo.). The blots were then probed with the second antibody as indicated in FIGS. 2A–G under the following conditions: the antibody was diluted 1:1000 into about 40 ml of PBS containing 0.05 percent NP-40 and incubated about 50 minutes at room temperature. The blots were then washed three times in PBS containing 0.05 percent NP-40, and then exposed for about one minute to the ECL reagents (Amersham, Arlington Heights, Ill.) at room temperature.

Figure 2C:
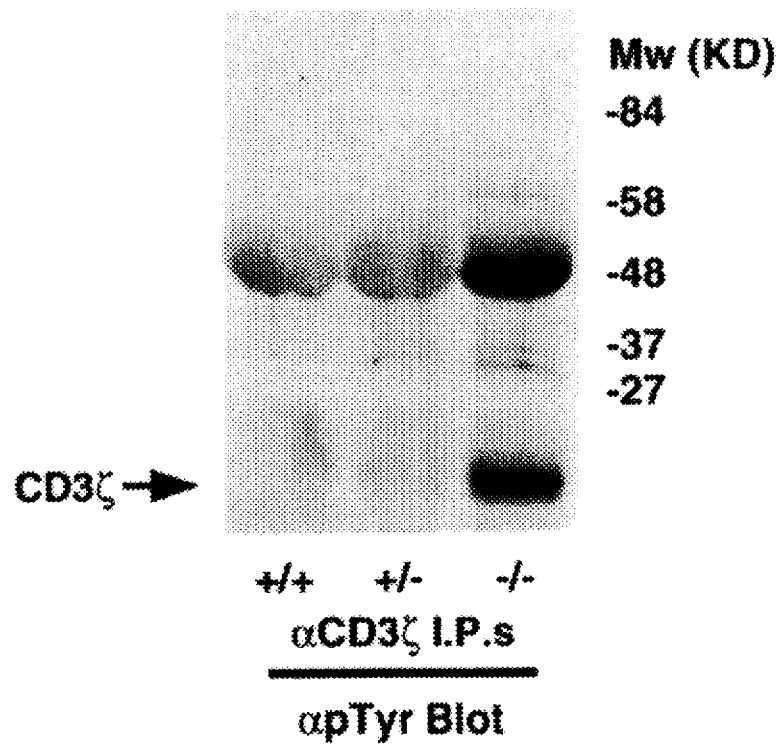
Figure 2D:
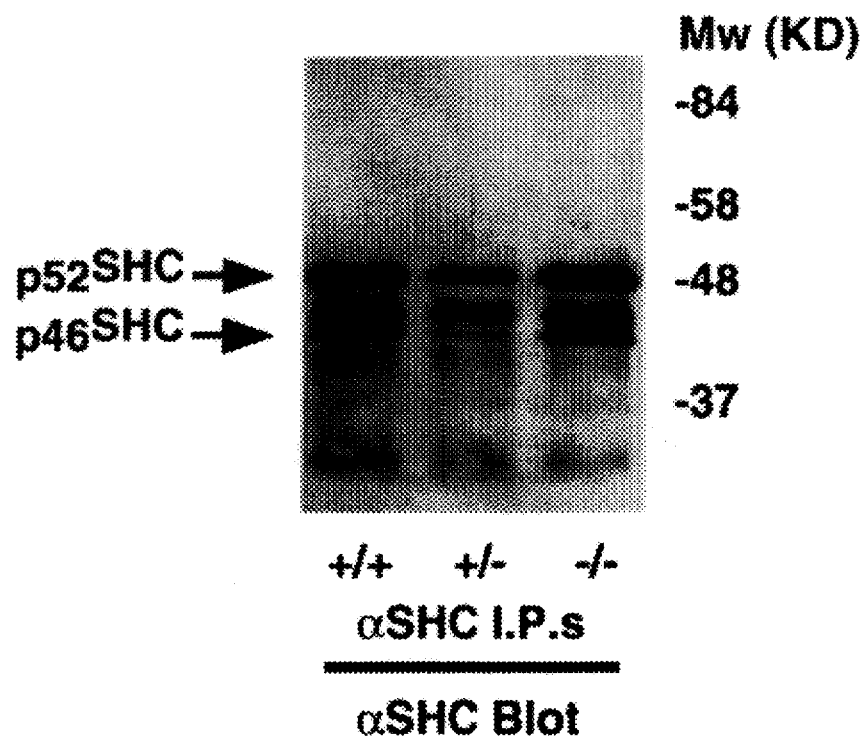
Figure 2E:
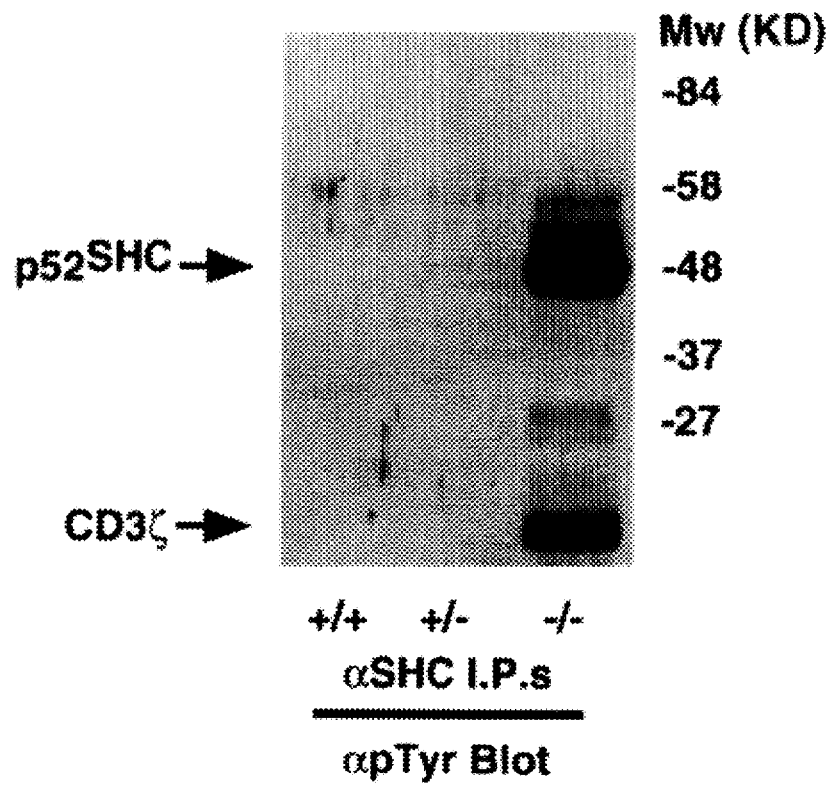
Figure 2F:
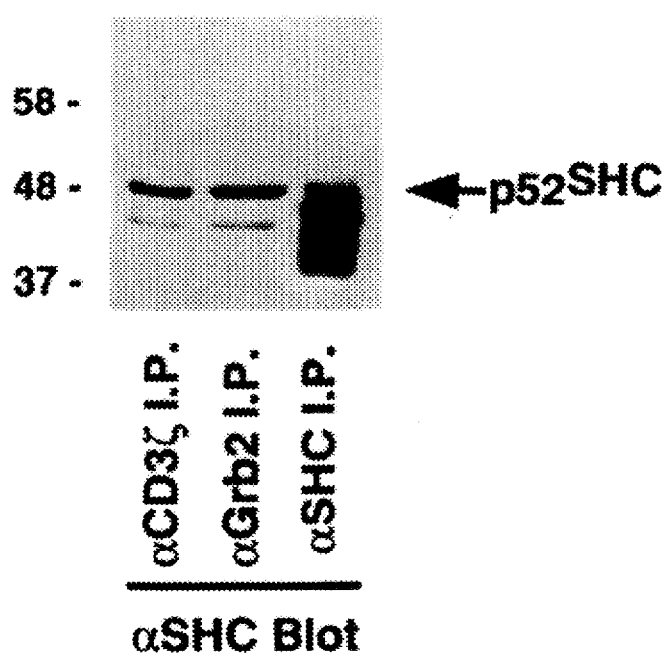
Figure 2G:
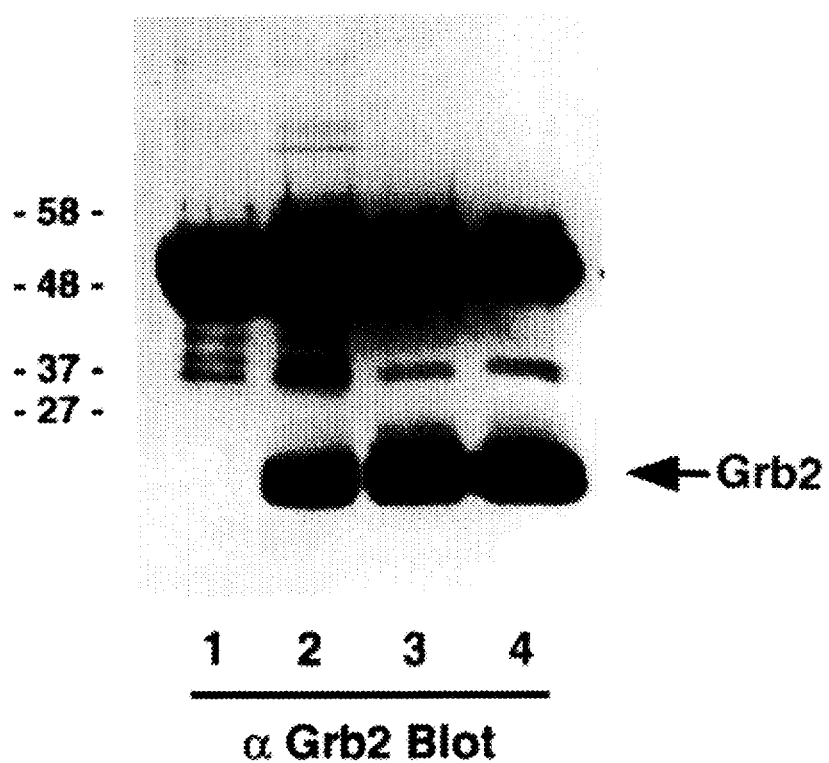

FIG. 2A shows that tyrosine phosphorylation of two proteins of approximate molecular weight 16 and 50 kD is significantly increased in T-cells obtained from CTLA-4 receptor knockout mice (i.e., T-cells not expressing CTLA-4 receptor). Increased tyrosine phosphorylation of three other proteins (about 140, 36, and 23 kD) is also increased, but to a much lesser extent. Further, as shown in FIGS. 2B and 2C, the two proteins have been identified by antibody binding analysis to be p52SHC and CD3ζ. In addition, tyrosine-phosphorylated p52SHC co-immunoprecipitated with tyrosine phosphorylated CD3ζ and Grb2 from CTLA-4 receptor homozygous knockout T-cells, but not from CTLA-4 receptor heterozygous or wild type T-cells, suggesting that TCR signaling is constitutively activated in CTLA-4 receptor homozygous knockout T-cells. FIG. 2D shows that comparable levels of protein were used in all immunoprecipitations. FIG. 2E indicates that detectable levels of CD3ζ bound to p52SHC in CTLA-4 knockout but not wild type cells. As is apparent in FIG. 2F, most of the phosphorylated p52SHC is associated with CD3ζ, as evidenced by the ability of CD3ζ to co-immunoprecipitate with p52SHC at levels similar to those observed in anti-Grb2 immunoprecipitate. FIG. 2G shows that the anti-CD3ζ immunoprecipitate (Lane 2) appears to be associated with Grb2 at levels approaching that of an anti-p52SHC immune complex (Lane 3). Lanes 1–4 in FIG. 2G correspond to anti-CD3ζ immunoprecipitate from CTLA-4 receptor wild type (Lane 1) and knockout (Lane 2) T cells, and anti-p52SHC immunoprecipitate from CTLA-4 receptor wild type (Lane 3) and knockout (Lane 4) T-cells.

To assess the relationship of CTLA-4 receptor with these other proteins, T-cells from a wild-type (i.e., expressing CTLA-4 receptor) mouse were prepared as described above and incubated on plates previously coated with anti-CD3 gamma antibodies (clone 145-2C11, Pharmingen, San Diego, Calif.) for about 48 hours in HL-1 medium (2 percent fetal calf serum, 2 mM glutathione). After 48 hours, the medium was removed and replaced with about 10 ml of HL-1 medium containing IL-2. Cells were harvested two days later. After harvesting, the cells were lysed in TNE buffer (see above), and the cleared lysates were incubated with hamster monoclonal anti-CTLA-4 receptor antibody (clone UC10-4F10-11, Pharmingen, San Diego, Calif.), rabbit polyclonal SYP antibodies (Signal Transduction Laboratories), mouse monoclonal SHP antibody (Signal Transduction Laboratories), rabbit polyclonal HePTP antibody, rabbit polyclonal PTP-PEST antibody (Pharmingen, San Diego, Calif.), or rabbit polyclonal CD3 zeta (clone 145-2C11, Pharmingen, San Diego, Calif.). The antibody-antigen complexes were precipitated using Sepharose beads (Protein-A Sepharose beads for rabbit polyclonal antibodies; Protein-G Sepharose beads for hamster antibodies; and anti-mouse IgG-agarose beads for mouse antibodies). The immunoprecipitated complexes were then separated by SDS-PAGE, and transferred on to nitrocellulose paper using standard Western blot procedures. Each antibody-antigen complex was Western blotted onto a separate nitrocellulose paper. The Western blots were then divided into individual strips, and each strip was then incubated with the indicated antibodies:

1) anti-SYP blot: anti-CTLA-4 receptor, anti-CD3, or anti-SYP immunoprecipitates;
2) anti-SHP blot: anti-CTLA-4 receptor or anti-SHP immunoprecipitates;
3) anti-HePTP blot: anti-CTLA-4 receptor or anti-HePTP immunoprecipitates; and
4) anti-PTP-PEST blot: anti-CTLA-4 receptor or anti-PTP-PEST immunoprecipitates.

After antibody incubation and rinsing using standard protocols, antibody binding to the Western blots was visualized using a second antibody directed to the first, where the second antibody was linked to HRP. HRP activity was then detected by enhanced chemiluminescence ("ECL", Amersham, Arlington Heights, Ill.).

Figures 1, 3A:
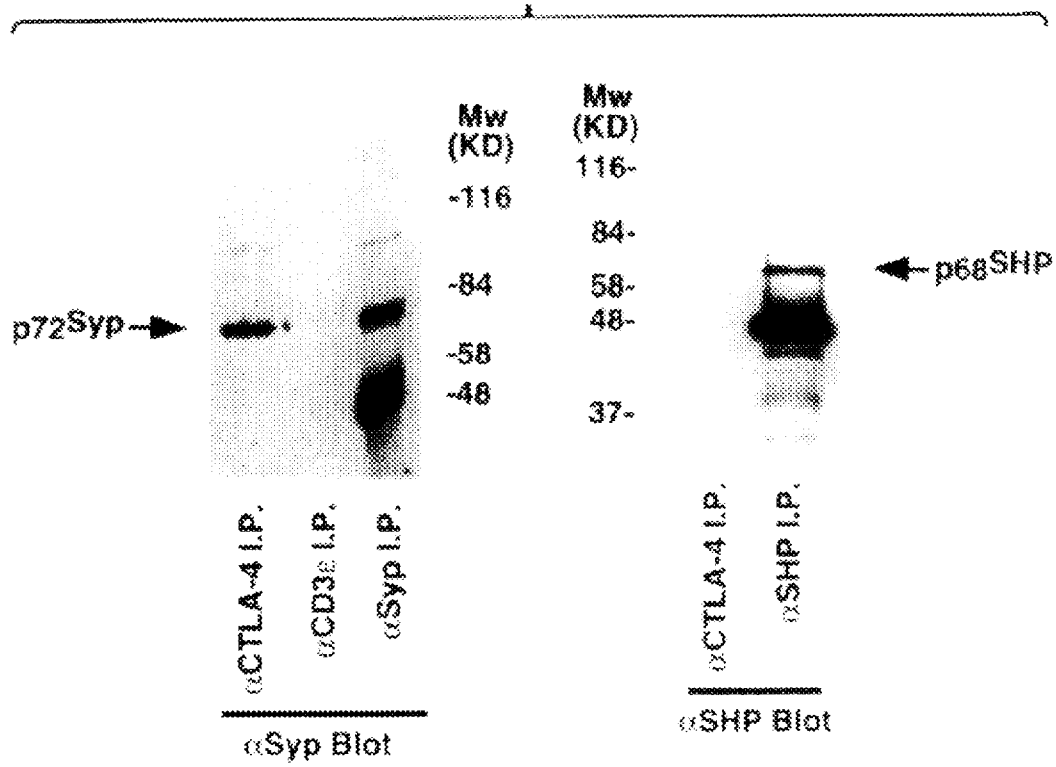
FIGS. 3A–3E depict a series of Western blots. "GST" refers to glutathione-S-transferase; all other abbreviations are as described for FIGS. 2A–2G. The lanes in 3E are described in Example II.
Figures 2, 3A:
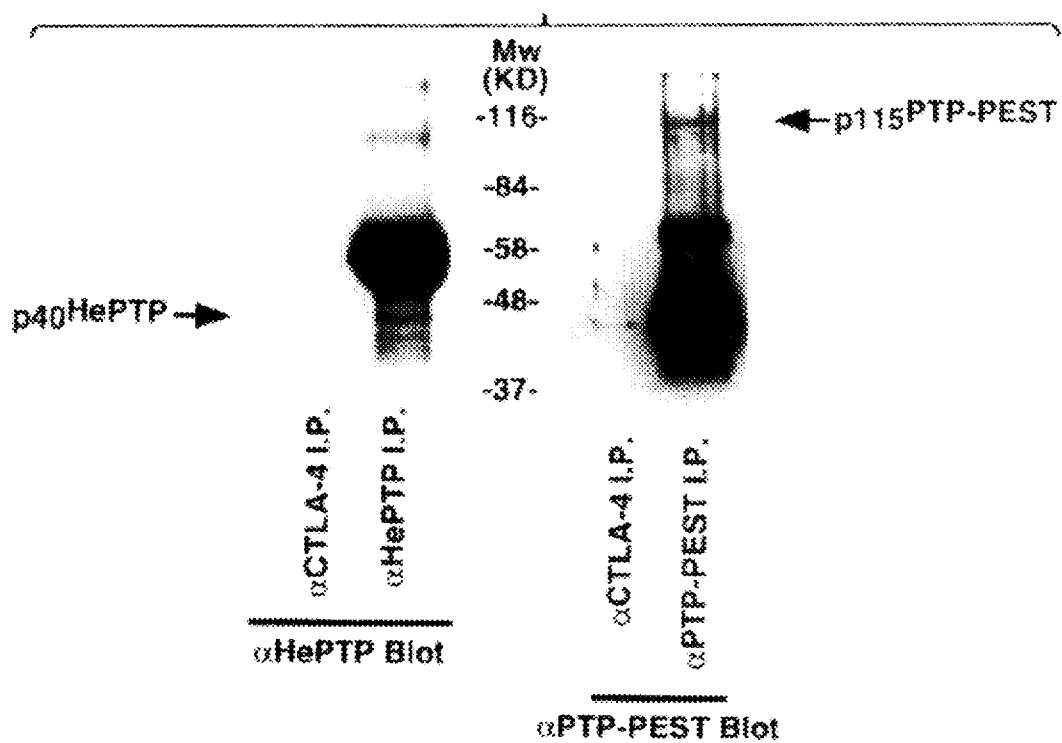

The results, shown in FIG. 3A, indicate that the SH2 domain-containing SYP specifically associates with CTLA-4 receptor.

Figure 3B:
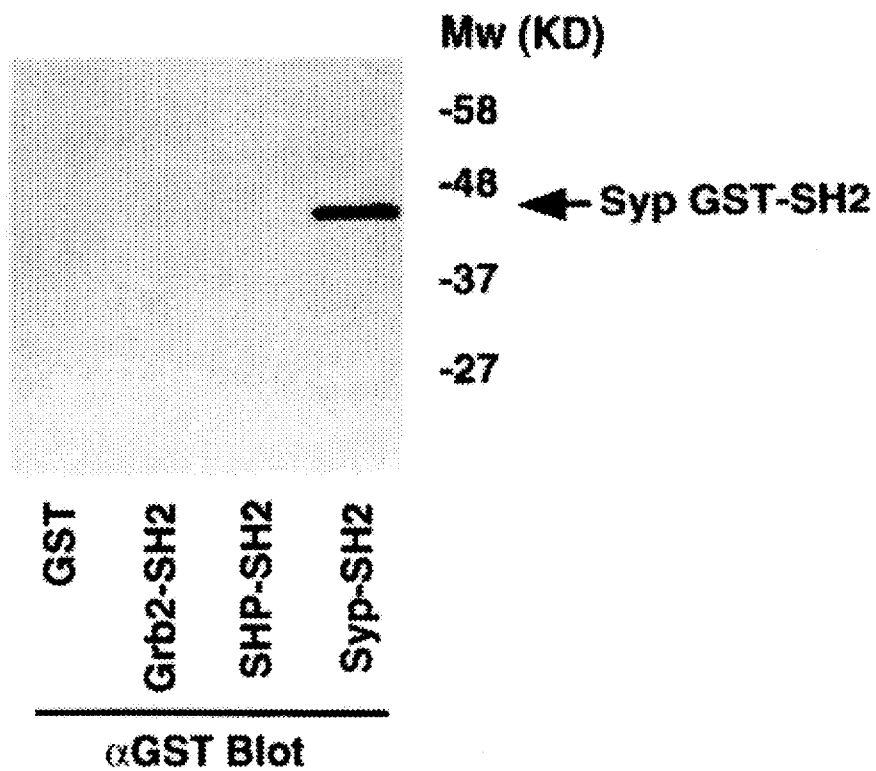

The cytoplasmic tail (carboxy terminus) of CTLA-4 receptor contains two potential sites for tyrosine-phosphorylation, i.e., Tyr201 and Tyr218. In order to identify which of these sites in fact associates with SYP, a GST fusion protein expressing the SH2 domains of SYP was prepared using the pGEX GST Gene Fusion Vector System (Life Technologies, Grand Island, N.Y.) by inserting into the vector a truncated DNA fragment of SYP encoding residues 2–216. The fusion protein was expressed and purified by following the manufacturer's protocol. The results, shown in FIG. 3B, indicate that the SH2 domains of SYP interact and immunoprecipitate with CTLA-4 receptor.

To further investigate the specificity of this interaction, synthetic biotinylated peptides corresponding to cytoplasmic sequences of CTLA-4 receptor were synthesized using standard methods and immobilized to a plate via streptavidin agarose beads. The sequence of each peptide was:

KMLKKRSPLTTGVYVKMPPTEPECEKQFQ
PYFIPIN  (SEQ ID NO: 1)

KQFQPYFIPIN  (SEQ ID NO: 2)

For SEQ ID NO: 1, two versions of this peptide were prepared, one in which the first tyrosine (Tyr201) was synthesized as a phosphotyrosine, and one in which is was not.

Figure 3C:
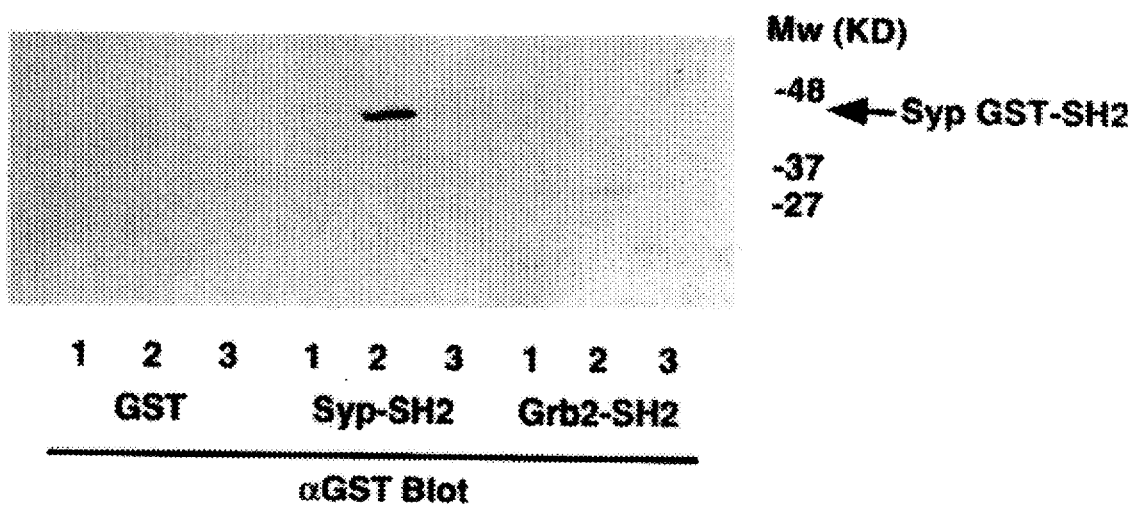

Approximately 1 µM of each peptide was incubated with about 5 µM of GST alone, GST-SYP SH2 domain fusion protein, or GST-Grb2 SH2 domain fusion protein. After incubation, the complexes were washed, separated, transferred, immunoblotted with anti-GST antibodies linked to HRP, and visualized. The results, shown in FIG. 3C, indicate that the GST-SYP SH2 domain fusion protein specifically binds to the CTLA-4 receptor fusion peptide Tyr201, where Tyr201 is phosphorylated.

Figure 3D:
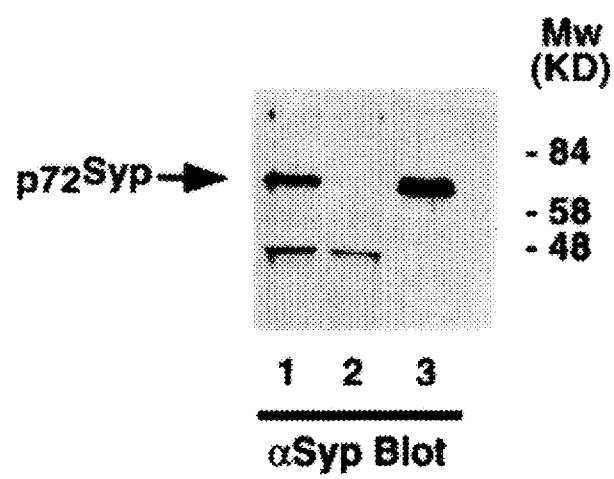

The sensitivity of the CTLA-4/SYP complex to tyrosine dephosphorylation was examined as follows. Activated CTLA-4 receptor wild type T-cells were lysed in TNE buffer as described above and CTLA-4 receptor was immunoprecipitated. The immunoprecipitate was washed three times with TNE buffer and then divided into aliquots. One aliquot was left untreated (FIG. 3D, Lane 1), and another aliquot was incubated in phosphatase buffer (20 mM Hepes pH 7.0, 5 percent glycerol, 0.05 percent Triton X-100, 2.5 mM magnesium chloride, 10 µg/µl Aprotinin, and leupeptin) at about 37° C. for about 1 hour (FIG. 3D, Lane 2). An anti-SYP immunoprecipitate was included as a control (FIG. 3D, Lane 3). The resulting complexes were passed through SDS-PAGE, Western blotted, and then probed with an anti-SYP antibody. As can be seen in FIG. 3D, phosphatase treatement of CTLA-4 receptor abrogated the ability of SYP to remain complexed with CTLA-4 receptor.

Figure 3E:
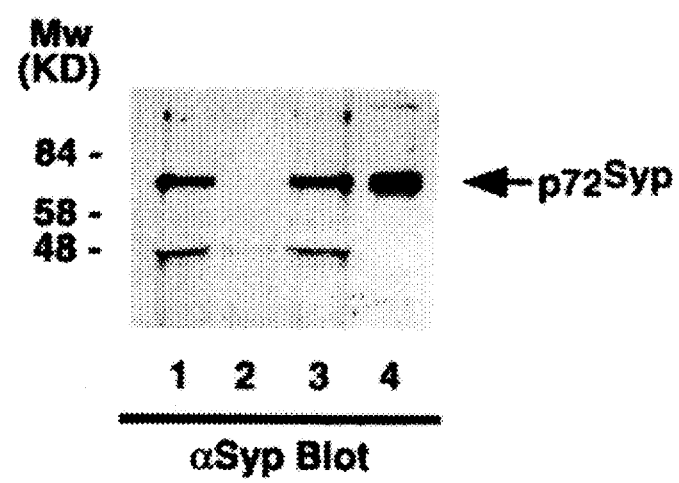

Two peptides were tested to evaluate their effect on the CTLA-4/SYP complex. CTLA-4 receptor was immunoprecipitated as described above, and the immunoprecipitates were then incubated with either no peptide (FIG. 3E, Lane 1), with the peptide YVKM (SEQ ID NO: 3) (FIG. 3E, Lane 2), or the peptide YFIP (SEQ ID NO: 4) (FIG. 3E, Lane 3) for about 1 hour at about 40° C. An anti-SYP immunoprecipitate was used as a positive control (FIG. 3E, Lane 4). After incubation, the immune complexes were washed, separated by SDS-PAGE, Western blotted, and probed with an anti-SYP antibody. As can be seen in FIG. 3E, the YVKM (SEQ ID NO: 3) peptide abrogated the ability of SYP to remain complexed with CTLA-4 receptor.

Figure 4A:
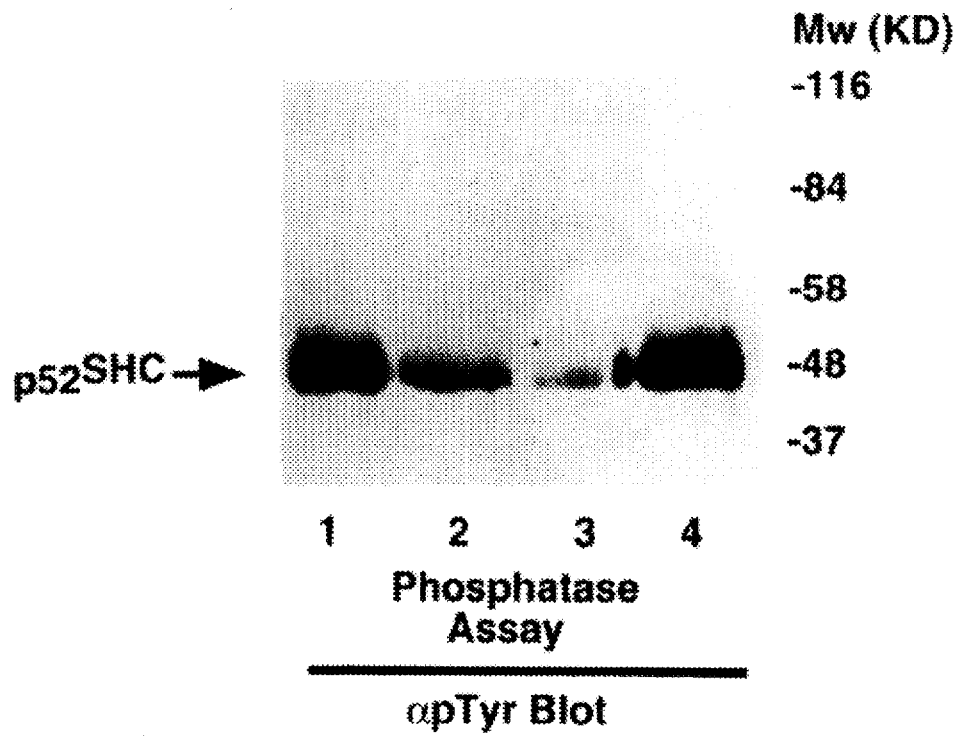
FIGS. 4A–4B depict two Western blots. The abbreviations are as described in FIGS. 1A–1C.
Figure 4B:
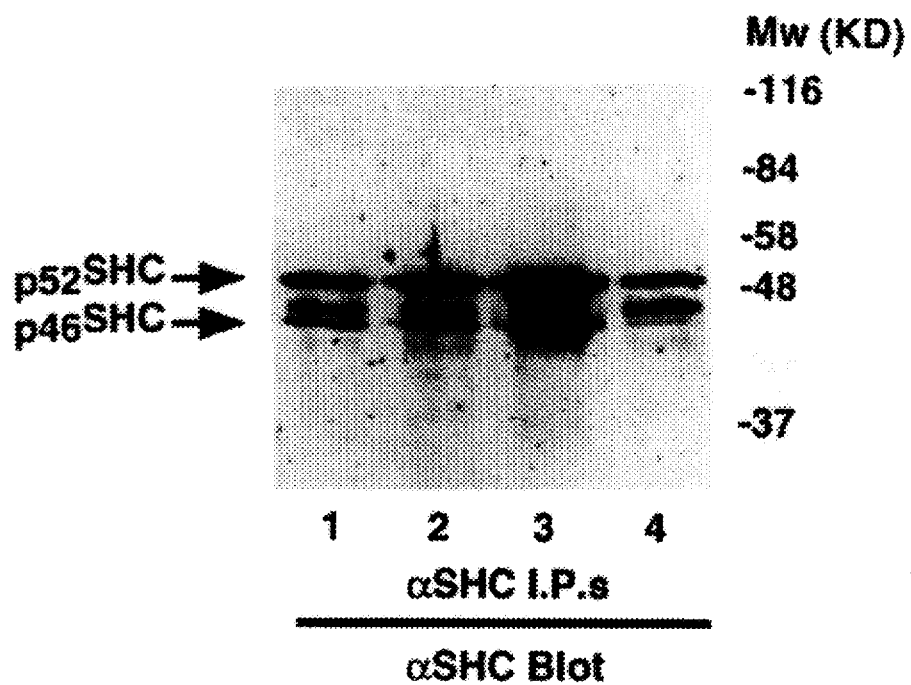

To further characterize the role of CTLA-4 receptor with respect to SYP and p52SHC, activated lymphocytes (prepared as described above) obtained from wild type mice (i.e., mice expressing CTLA-4 receptor on T-cells) were lysed, incubated with either anti-CTLA-4 receptor antibodies or anti-SYP antibodies (see above), and then immunoprecipitated. The anti-CTLA-4 receptor immunoprecipitate was divided into two aliquots; one aliquot was washed with TNE buffer, and the other was heat denatured in 2 percent SDS. Both of these aliquots and the anti-SYP immunoprecipitate were then washed with phosphatase buffer (20 mM Hepes, pH 7.0, 5 percent glycerol, 0.05 percent Triton X-100, 2.5 mM magnesium chloride, 10 µg/ml of each of Aprotinin and Leupeptin). Separately, a lysate was prepared from lymphocytes derived from CTLA-4 receptor deficient mice, and tyrosine phosphorylated p52SHC was immunoprecipitated from this lysate as described above. After washing in phosphatase buffer, this p52SHC was divided into four aliquots and added to the two anti-CTLA-4 receptor immunoprecipitates and the anti-SYP immunoprecipitate. All mixtures were incubated about 1 hour at about 37° C. The resulting complexes were washed with TNE buffer, separated by SDS-PAGE, transferred to a membrane, immunoanalyzed by Western blotting using anti-phosphotyrosine antibodies. The level of p52SHC phosphorylation was visualized using an anti-phosphotyrosine antibody linked to HRP. As shown in FIG. 4A, both the CTLA-4 receptor bound SYP and immunoprecipitated SYP (Lanes 2 and 3, respectively; Lane 1, the control, contained p52SHC and buffer only), but not the SDS-denatured CTLA-4 receptor immune complex (Lane 4), dephosphorylated p52SHC. FIG. 4B shows that equal amounts of p52SHC were added to all samples.

We claim:

1. A method of identifying a test molecule that inhibits SYP binding to a phosphorylated CTLA-4 receptor in vitro comprising contacting the test molecule with SYP in the presence of phosphorylated CTLA-4 receptor, and assaying in a T-cell for a decrease in SYP binding to phosphorylated CTLA-4 receptor as compared with the level of SYP binding to phosphorylated CTLA-4 receptor in the absence of a test molecule, wherein a decrease in SYP binding indicates the presence of a molecule which inhibits SYP binding to a phosphorylated CTLA-4 receptor.

2. The method of claim 1 wherein the molecule is an inorganic molecule.

3. The method of claim 1 wherein the molecule is an organic molecule.

4. The method of claim 3 wherein the molecule is naturally occurring.

5. The method of claim 3 wherein the molecule is synthetically produced.

6. A method of identifying a test molecule that inhibits SYP binding to a phosphorylated CTLA-4 receptor in vitro comprising contacting the test molecule with SYP in the presence of phosphorylated CTLA-4 receptor and phosphorylated p52SHC, and assaying in a T-cell for decreased dephosphorylation of p52SHC as compared with the level of dephosphorylation of p52SHC in the absence of a test molecule, wherein a decrease in dephosphorylation of p52SHC indicates the presence of a molecule which inhibits SYP binding to a phosphorylated CTLA-4 receptor.

7. The method of claim 6 wherein the molecule is an inorganic molecule.

8. The method of claim 6 wherein the molecule is an organic molecule.

9. The method of claim 8 wherein the molecule is naturally occurring.

10. The method of claim 8 wherein the molecule is synthetically produced.

11. A method of identifying a test molecule that inhibits SYP binding to a phosphorylated CTLA-4 receptor in vitro comprising contacting the test molecule with SYP in the presence of phosphorylated CTLA-4 receptor, and assaying for a decrease in SYP binding to phosphorylated CTLA-4 receptor as compared with the level of SYP binding to phosphorylated CTLA-4 receptor in the absence of a test molecule, wherein a decrease in SYP binding indicates the presence of a molecule which inhibits SYP binding to a phosphorylated CTLA-4 receptor.

12. A method of identifying a test molecule that inhibits SYP binding to a phosphorylated CTLA-4 receptor in vitro comprising contacting the test molecule with purified SYP protein in the presence of purified phosphorylated CTLA-4 receptor protein, and assaying in a T-cell for a decrease in SYP binding to phosphorylated CTLA-4 receptor as compared with the level of SYP binding to phosphorylated CTLA-4 receptor in the absence of a test molecule, wherein a decrease in SYP binding indicates the presence of a molecule which inhibits SYP binding to a phosphorylated CTLA-4 receptor.

13. A method of identifying a test molecule that inhibits SYP binding to a phosphorylated CTLA-4 receptor in vitro comprising contacting the test molecule with SYP in the presence of phosphorylated CTLA-4 receptor and phosphorylated p52SHC, and assaying for decreased dephosphorylation of p52SHC as compared with the level of dephosphorylation of p52SHC in the absence of a test molecule, wherein a decrease in dephosphorylation of p52SHC indicates the presence of a molecule which inhibits SYP binding to a phosphorylated CTLA-4 receptor.

14. A method of identifying a test molecule that inhibits SYP binding to a phosphorylated CTLA-4 receptor in vitro comprising contacting the test molecule with purified SYP protein in the presence of purified phosphorylated CTLA-4 receptor and purified phosphorylated p52SHC, and assaying for decreased dephosphorylation of p52SHC as compared with the level of dephosphorylation of p52SHC in the absence of a test molecule, wherein a decrease in dephosphorylation of p52SHC indicates the presence of a molecule which inhibits SYP binding to a phosphorylated CTLA-4 receptor.

* * * * *